(12) United States Patent
Boudy et al.

(10) Patent No.: US 9,925,266 B2
(45) Date of Patent: Mar. 27, 2018

(54) GELLING FORMULATION BASED ON CALCIUM GLUCONATE

(71) Applicant: Assistance Publique—Hopitaux De Paris, Paris (FR)

(72) Inventors: Vincent Boudy, Paris (FR); Sandrine Graff De Faget, La Celle Saint Cloud (FR); Marie-Caroline Husson, Paris (FR); Imane Boucenna, Maisons-Alfort (FR); Laurent Royon, Paris (FR); Pierre Colinart, Clamart (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 149 days.

(21) Appl. No.: 14/381,316

(22) PCT Filed: Feb. 27, 2013

(86) PCT No.: PCT/IB2013/051565
§ 371 (c)(1),
(2) Date: Aug. 27, 2014

(87) PCT Pub. No.: WO2013/128383
PCT Pub. Date: Sep. 6, 2013

(65) Prior Publication Data
US 2015/0005380 A1    Jan. 1, 2015

(30) Foreign Application Priority Data
Feb. 27, 2012  (FR) ..................... 12 51758

(51) Int. Cl.
| | |
|---|---|
| *A61K 47/32* | (2006.01) |
| *A61K 47/10* | (2017.01) |
| *A61K 9/06* | (2006.01) |
| *A61K 31/191* | (2006.01) |
| *A61K 9/14* | (2006.01) |
| *A61L 9/12* | (2006.01) |
| *A61K 9/00* | (2006.01) |
| *A61L 26/00* | (2006.01) |
| *A61K 9/70* | (2006.01) |
| *A61K 31/7004* | (2006.01) |
| *A61K 9/12* | (2006.01) |

(52) U.S. Cl.
CPC ............ *A61K 47/32* (2013.01); *A61K 9/0014* (2013.01); *A61K 9/06* (2013.01); *A61K 9/12* (2013.01); *A61K 9/7015* (2013.01); *A61K 31/191* (2013.01); *A61K 31/7004* (2013.01); *A61K 47/10* (2013.01); *A61L 26/008* (2013.01); *A61L 26/0019* (2013.01); *A61L 26/0066* (2013.01)

(58) Field of Classification Search
CPC ............ A61L 26/0019; A61L 26/0066; A61L 26/008; C08L 71/02; A61K 31/191; A61K 31/7004; A61K 47/10; A61K 47/32; A61K 9/06; A61K 9/12; A61K 9/7015

See application file for complete search history.

(56) References Cited

U.S. PATENT DOCUMENTS

2005/0079147 A1*  4/2005  Delaey .................. A61K 31/74
                                                  424/78.08
2011/0230566 A1*  9/2011  Tamargo ................ A61K 8/315
                                                  514/759

FOREIGN PATENT DOCUMENTS

| EP | 0 134 964 A2 | 3/1985 |
| EP | 0 551 626 A1 | 7/1993 |
| EP | 2 145 617 A1 | 1/2010 |

OTHER PUBLICATIONS

International Search Report and Written Opinion from International Application No. PCT/IB2013/051565, dated Jun. 5, 2013.
Orion Laboratories: "Calcium Gluconate Gel 2.5%"; Retrieved from the Internet: URL:http://www.orion.net.au/products/pdf/cal01466_msds.pdf [retrieved on Jul. 16, 2012]; Nov. 1, 2011; pp. 1-3; XP055032874.
Develay P et al: "Use of a Calcium Gluconate Gel for Treatment of Skin Burns Caused by Fluorhydric Acid"; Journal de Pharmacie Clinique; 1983 FR; vol. 2, No. 2; 1983; pp. 115-122; XP009161159.
Roblin I et al: "Topical Treatment of Experimental Hydrofluoric Acid Skin Burns by 2.5% Calcium Gluconate"; Journal of Burn Care and Research; vol. 27, No. 6; Nov. 2006; pp. 889-894; XP009161161.
Henry R L et al: "Burn Wound Coverings and the Use of Poloxamer Preparations"; Critical Reviews in Biocompatibility; CRC Press, Boca Raton, FL, US; vol. 5, No. 3; Jan. 1, 1989; pp. 207-220; XP009031663.
Schmolka I R: "Artificial Skin I. Preparation and Properties of Pluronic F-127 Gels for Treatment of Burns"; Journal of Biomedical Materials Research; Wiley, New York, US; vol. 6, No. 6; Nov. 1, 1972; pp. 571-582; XP009017693.
Nalbandian R M et al: "Pluronic F-127 Gel Preparation as an Artificial Skin in the Treatment of Third-Degree Burns in Pigs"; Journal of Biomedical Materials Research; Wiley, New York, US; vol. 21, No. 9; Sep. 1, 1987; pp. 1135-1148; XP002915634.

* cited by examiner

*Primary Examiner* — Sreeni Padmanabhan
*Assistant Examiner* — Jody Karol
(74) *Attorney, Agent, or Firm* — Alston & Bird LLP

(57) ABSTRACT

The invention related to a gelling formulation including calcium gluconate in solution in water and a poloaxmer and to the use thereof in the treatment of hydrofluoric acid burns.

12 Claims, No Drawings

GELLING FORMULATION BASED ON CALCIUM GLUCONATE

FIELD

The invention relates to a gelling formulation based on calcium gluconate, to the use thereof in the treatment of hydrofluoric acid burns and to the process for preparing the same.

BACKGROUND

Hydrogen fluoride (HF) is a colorless fuming liquid or else a gas with a strong, irritating odor, which is extremely corrosive. Hydrofluoric acid is an aqueous solution of hydrogen fluoride. It is a strong acid which has highly caustic and corrosive effects on organic tissues, owing to the dissociated fluoride ions ($F^-$).

Hydrofluoric acid is mainly used in industry as a raw material, in particular in the manufacture of stainless steel, of aluminum or of organic or inorganic chemical products, in oil refining, and in the manufacture of glass and of electronic components. Hydrofluoric acid is also present in various domestic products (for example antirust products). Consequently, the risk of exposure to hydrofluoric acid involves a large population of individuals.

Hydrofluoric acid can cause serious and painful burns on the skin and eyes. The symptoms, which are generally delayed and localized with dilute solutions of hydrofluoric acid, comprise erythema, edema and pain. As for the other acids, the seriousness of the burns depends on the concentration and on the temperature of the hydrofluoric acid and also on the exposure time. However, hydrofluoric acid differs from the other acids in that the fluoride ions rapidly penetrate the skin, thus being able to cause deep tissue destruction, soft tissue necrosis, tendinitis, tenosynovitis or bone decalcification. Contrary to other acids which can be rapidly neutralized, this process can continue for days if it is not treated.

There are several types of treatment for hydrofluoric acid burns, among which mention may be particularly made of the topical application of a magnesium oxide-ased paste[1] or else the injection of magnesium-based compounds such as magnesium sulfate or magnesium acetate[2].

Other treatments involve in particular the use of quaternary ammonium-based compounds[3] such as benzethonium chloride solution (Hyamine®)[3,4] or benzalkonium chloride (Zephiran®)[3,4]. However, treatment with Hyamine® requires saturating the burn area for a prolonged period.

Calcium gluconate-based infiltrations have for a long time been used to effectively treat hydrofluoric acid burns[1, 2, 4-7]. They make it possible to restrict the degree of edema or of necrosis caused by the hydrofluoric acid and prevent the fluoride ions from penetrating deeply. This laborious and invasive treatment is, however, generally reserved for cases of particularly serious burns, and is not suitable for giving first aid.

The gel based on calcium gluconate[8-12], in particular based on 2.5% of calcium gluconate, is moreover widely used in first aid for hydrofluoric acid burns. After rinsing with cold water, the gel is applied to the skin so as to prevent the injury from spreading. However, because of quite a limited demand, the calcium gluconate-based gel is not commercially available from the pharmaceutical laboratories. In France, this gel, which is also available in magistral preparation form, has the regulatory status of a hospital preparation. A ready-to-use gel based on carboxymethylcellulose/glycerol is thus manufactured and distributed by the Agence Générale des Produits de Santé [General Health Product Agency] (AGEPS, Paris, France). In the United States, this gel, which has not received approval from the Food and Drug Administration (FDA), is prepared extemporaneously by mixing calcium gluconate in solution or in powder form into a water-soluble lubricant. However, the absence of standardization of the preparation of the gel, and also the absence of stability and sterility tests, represent significant limiting factors for these noncommercial products. Moreover, these gel-type formulations do not allow wide distribution of the treatment. In addition, this distribution is generally carried out by hand or by means of a nonsterile spatula, which poses risks of microbial contamination.

SUMMARY

A novel formulation which makes it possible to overcome the drawbacks of the current treatments, and in particular of the calcium gluconate-based gel, has now been developed. More particularly, the invention relates to a calcium gluconate-based formulation advantageously capable of being sprayed in liquid form onto the burn and of instantaneously gelling on contact with the skin. Compared with a solution, the presence of a gel texture at the surface of the skin allows prolonged contact of the calcium gluconate with the injury. This formulation offers several advantages: it is first of all easy to apply and can be widely distributed on the burns to be treated; it can, moreover, be easily prepared and packaged so as to be stored under sterile conditions; this formulation is particularly stable over time and can be stored for several months. Finally, this formulation makes it possible to give first aid rapidly, safely and economically in cases of accidental hydrofluoric acid burns.

Thus, according to a first aspect, the invention relates to a gelling formulation comprising calcium gluconate in solution in water and a poloxamer.

DETAILED DESCRIPTION

For the purpose of the present description, the term "gelling formulation" is intended to mean a formulation capable of gelling, in particular in which the concentration of the poloxamer(s) is sufficient to allow the aqueous solution to gel at a given temperature, in particular on contact with the skin.

Calcium gluconate is the compound having the following structure:

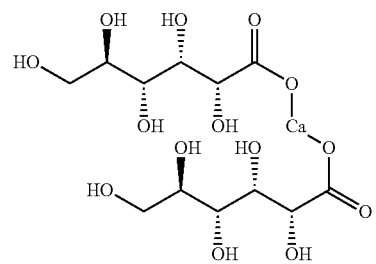

The avidity of fluoride ions for calcium ions so as to form insoluble salts forms the basis of calcium gluconate treatments for hydrofluoric acid burns.

The formulations according to the present application preferably comprise from 1% to 5% by weight of calcium gluconate, more preferentially approximately 2.5% by weight relative to the total weight of the formulation.

As it is used herein, the term "poloxamer" denotes a block copolymer comprising or consisting of a polyoxypropylene (also called polypropylene glycol, POP) central chain grafted on both sides with a polyoxyethylene (also called polyethylene glycol, POE) chain. Poloxamers are generally denoted by the letter "P" (for poloxamer) followed by three numbers: the first two numbers multiplied by 100 give the molecular weight of the polyoxypropylene core, and the last number multiplied by 10 gives the percentage of the polyoxyethylene content. By way of example, P407 corresponds to a poloxamer of which the polyoxypropylene core has a molecular weight of 4000 g/mol and a polyoxyethylene content of 70%.

The poloxamers which are of use according to the invention are thermosensitive poloxamers, which are in the liquid state at ambient temperature, in particular between 15 and 25° C., and in the gel state at a temperature greater than or equal to their gelling temperature ($T_g$), in particular under physiological conditions.

The gelling temperatures of poloxamers ($T_g$) can be determined according to conventional methods or are available in reference books such as the *Handbook of Pharmaceutical Excipients*.

More particularly, these poloxamers are present in a sufficient concentration in the aqueous solution of the calcium gluconate to allow its gelling when the temperature is greater than or equal to their gelling temperature ($T_g$), in particular under physiological conditions.

Preferably, the formulation gels at a temperature of between 27 and 37° C., more preferentially on contact with the skin, in particular at a temperature of between 31 and 34° C. The formulations according to the present application generally comprise from 10% to 30% by weight of poloxamer, preferably from 10 to 25% by weight relative to the total weight of the composition. As an example, mention may in particular be made of poloxamer 407, poloxamer 188 or a mixture thereof.

According to one preferred variant, the formulations according to the invention comprise approximately 2.5% by weight of calcium gluconate and approximately 13% to 16% by weight, in particular approximately 15% by weight of poloxamer 407, relative to the total weight of the composition. They may also comprise poloxamer 188, in an amount which can range in particular from 1% to 10% by weight, in particular from 1% to 6% by weight relative to the total weight of the composition.

The formulations according to the present application may also comprise excipients, in particular calcium gluconate-solubilizing agents such as propylene glycol or salts such as sodium chloride, or else bioadhesion agents such as hydroxypropylmethylcellulose, methylcellulose or cross-linked acrylic acid polymers.

According to one embodiment, the formulations according to the invention also comprise sodium chloride, in particular from 1% to 6% by weight of sodium chloride relative to the total weight of the composition.

According to one preferred variant, the formulations of the invention comprise approximately 15% by weight of poloxamer 407, approximately from 0 to 6% by weight of poloxamer 188 and approximately from 0 to 6% of sodium chloride, the weight percentages referring to the total weight of the composition.

Advantageously, the formulations according to the invention are sterile and can be prepared by sterilizing filtration, by radiosterilization, or else under aseptic conditions. More particularly, this solution can be prepared and/or stored under sterile conditions in a bottle equipped with a suitable sprayer.

According to another aspect, the invention relates to a pharmaceutical composition comprising or consisting of a gelling formulation as defined above.

According to yet another aspect, the invention relates to a gelling formulation as defined above, for use in the treatment of skin burns caused by hydrofluoric acid, intended in particular to be administered topically, on the burn.

Preferably, the formulation according to the present application is sprayed onto the skin, and instantaneously forms a gel on the area of application.

According to another aspect, the invention relates to a method for preparing a gelling formulation as defined above, said method comprising the steps of:
 i) Cold-dissolution of the poloxamer in water;
 ii) Addition and dissolution of the calcium gluconate in the solution obtained in step i) previously brought to a temperature between 60° C. and 90° C.; and, optionally
 iii) Recovery of the formulation obtained.

According to one alternative, the method comprises the steps of:
 i) Dissolution of the calcium gluconate in water at a temperature of between 60° C. and 90° C.; and
 ii) Addition and dissolution of the poloxamer in the solution obtained in step i) which has been previously cooled, in particular to a temperature between 15 and 25° C.; and, optionally
 iii) Recovery of the formulation obtained.

Definitions

As it is used in the present description, the term "approximately" refers to a range of values of ±10% of a specific value. By way of example, the expression "approximately 16%" comprises the values of 16% ±10%, i.e. the values from 14.4% to 17.6%.

For the purpose of the present description, the percentages refer to percentages by weight relative to the total weight of the formulation, unless otherwise indicated.

As it is intended herein, the value ranges in the form of "x-y" or "from x to y" or "between x and y" include the limits x and y and also the integers comprised between these limits. By way of example, "1-6" or "from 1 to 6" or "between 1 and 6" denotes the integers 1, 2, 3, 4, 5 and 6. The preferred embodiments include each integer taken individually in the value range, and also any subcombination of these integers. By way of example, the preferred values for "1-6" may comprise the integers 1, 2, 3, 4, 5, 6, 1-2, 1-3, 1-4, 1-5, 2-3, 2-4, 2-5, 2-6, etc.

EXAMPLES

Example 1

Preparation of a Gelling Formulation Containing 2.5% of Calcium Gluconate (Method A)

16 g of poloxamer 407 (Lutrol®, BASF) were dissolved under cold conditions, i.e. at ambient temperature, in 81.5 ml of water. The solution obtained was then heated to approximately 80° C. and then 2.5 g of calcium gluconate were added and dissolved by stirring for approximately one hour.

The solution obtained gels on contact with the skin.

Example 2

Preparation of a Gelling Formulation Containing 2.5% of Calcium Gluconate (Method B)

2.5 g of calcium gluconate were dissolved with stirring in 81.5 ml of water preheated to 80° C. The solution obtained was then cooled to ambient temperature before the addition of 16 g of poloxamer 407.

The solution obtained gels on contact with the skin.

Example 3

The formulations reported in the table below were prepared according to methods A and B above.

The osmolarity is between 600 and 1000 mOsm/Kg.

|  | Calcium gluconate (w/w) | P.407 (w/w) | P.188 (w/w) | NaCl (w/V) | Gelling T° C. | Stability |
|---|---|---|---|---|---|---|
| 111227B | 2.6% | 15% | 3% | 4% | 39 to 32° C. | Clear (−) |
| 111222B | 2.6% | 15% | 6% | 5% | 38.8 to 31.8° C. | Clear |
| 111227C | 2.6% | 15% | 6% | 4% | 39 to 29.4° C. | Clear (++) |
| 120104A | 2.6% | 16% |  |  | 37.8 to 28° C. | Two-phase system |
| 120104B | 2.6% | 16% |  | 2% | 32.9 to 24.5° C. | Clear |
| 120104C | 2.6% | 16% | 1% | 2% | 39.8 to 29.8° C. | Clear (++) |

REFERENCES

[1]. Jones A T., *J Ind. Hyg. Toxicol*, 1939, 21:205.
[2]. Harris J C, Rumack B H, Bregman D J., *Clin. Toxicol*, 1981, 18:1027-1032.
[3]. Reinhardt C F, Hume W G, Linch A L, Wetherhold J M, *Am. Ind. Hyg. Assoc. J.*, 1, 1966, 27:166-171.
[4]. Dibbell D G, Iverson R E, Jones W J, Laub D R, Madison M S, *J. Bone Joint Surg.*, 1970, 52:931-936.
[5]. Paley and Seifter, *Proc. Soc. Exp. Biol. Med.*, 1941, 46:190.
[6]. Iverson R E, Laub D R, Madison M S, *Plast. Reconstr. Surg.*, 1971, 48:107-112.
[7]. Velvart J., *Hum. Toxicol*, 1983, 2:233-238.
[8]. Browne T D, *J. Soc. Occup. Med.*, 1974, 24:80-89.
[9]. Bracken W M, Cuppage F, McLaury R L, Kirwin C, Klassen C D, *J. Occup. Med.*, 1985, 27:733-739.
[10]. Kodoma Y, Matsuno K, Kayama F, Suenaga R, *Jpn J Ind. Health*, 1988, 30:400-401.
[11]. Kono K, Yoshida Y, Watanabe M, et al., *Recent advances in researches on the combined effects of environmental factors*, Kasuya M ed, Toyama Japan: Chuetsu Co Ltd, 1994:407-413.
[12]. Roblin I., Urban M, Flicoteau D., Martin C., Pradeau D., *J. Burn. Care Res.*, 2006 Nov-Dec; 27(6): 889-94.

The invention claimed is:

1. A gelling formulation comprising calcium gluconate in solution in water, from 13% to 17.6% by weight of poloxamer 407 and from 1% to 6% by weight of poloxamer 188, relative to the total weight of the formulation, wherein
said formulation gels on contact with the skin,
said formulation does not gel below 27° C.

2. The gelling formulation as claimed in claim 1, comprising from 1% to 5% by weight of calcium gluconate relative to the total weight of the formulation.

3. The gelling formulation as claimed in claim 1, also comprising sodium chloride.

4. The gelling formulation as claimed in claim 1, wherein the gelling formulation is sterile.

5. A pharmaceutical composition comprising the gelling formulation as claimed in claim 1.

6. The gelling formulation as claimed in claim 1, for use in the treatment of skin burns caused by hydrofluoric acid.

7. The gelling formulation for use as claimed in claim 6, wherein the gelling formulation is sprayed onto the skin.

8. A method for preparing a gelling solution as claimed in claim 1, said method comprising the steps of:
   i) cold-dissolutioning of the poloxamer 407 and the poloxamer 188 in water;
   ii) adding and dissolution of the calcium gluconate in the solution obtained in step i) brought to a temperature of between 60° C. and 90° C.

9. A method for preparing a gelling solution as claimed in claim 1, said method comprising the steps of:
   i) dissolutioning of the calcium gluconate in water at a temperature of between 60° C. and 90° C.; and
   ii) adding and dissolution of the poloxamer 407 and the poloxamer 188 in the solution obtained in step i) which has been previously cooled.

10. The gelling formulation as claimed in claim 1, comprising approximately 2.5% by weight of calcium gluconate relative to the total weight of the formulation.

11. A method for the treatment of skin burns caused by hydrofluoric acid, comprising applying the gelling formulation as claimed in claim 1 to a skin burn caused by hydrofluoric acid.

12. The method of claim 11, wherein the step of applying the gelling formulation comprises spraying the gelling formulation onto the skin.

* * * * *